United States Patent
Choi et al.

(10) Patent No.: US 8,229,765 B2
(45) Date of Patent: Jul. 24, 2012

(54) AUTOMATICALLY ASSESSING DRUG INTERACTIONS WHILE PROTECTING PATIENT PRIVACY

(75) Inventors: Christopher Y. Choi, Southport (AU); Christopher J. Hockings, Burleigh Waters (AU); Neil I. Readshaw, Parkwood (AU)

(73) Assignee: International Business Machines Corporation, Armonk, NY (US)

( * ) Notice: Subject to any disclaimer, the term of this patent is extended or adjusted under 35 U.S.C. 154(b) by 371 days.

(21) Appl. No.: 12/428,539

(22) Filed: Apr. 23, 2009

(65) Prior Publication Data

US 2010/0274586 A1    Oct. 28, 2010

(51) Int. Cl.
  *G06Q 50/00*    (2006.01)
(52) U.S. Cl. ................................. 705/3; 705/2
(58) Field of Classification Search .................... 705/2–3
  See application file for complete search history.

(56) References Cited

U.S. PATENT DOCUMENTS

| | | | |
|---|---|---|---|
| 5,758,095 A | 5/1998 | Albaum et al. | |
| 6,317,719 B1 * | 11/2001 | Schrier et al. | 705/2 |
| 6,401,085 B1 * | 6/2002 | Gershman et al. | 1/1 |
| 6,988,075 B1 * | 1/2006 | Hacker | 705/3 |
| 2002/0128863 A1 * | 9/2002 | Richmond | 705/2 |
| 2002/0165852 A1 | 11/2002 | Gogolak | |
| 2006/0265245 A1 | 11/2006 | McCallie et al. | |
| 2007/0074043 A1 * | 3/2007 | Lacey | 713/186 |
| 2007/0179812 A1 * | 8/2007 | Chapman | 705/3 |
| 2008/0010088 A1 | 1/2008 | Ben-Attar et al. | |
| 2008/0071577 A1 * | 3/2008 | Highley | 705/3 |
| 2008/0183504 A1 * | 7/2008 | Highley | 705/3 |

* cited by examiner

*Primary Examiner* — Gerald J. O'Connor
*Assistant Examiner* — Sind Phongsvirajati
(74) *Attorney, Agent, or Firm* — Yee & Associates, P.C.; Jeffrey S. LaBaw

(57) ABSTRACT

A drug interaction utility can retrieve the patient's current medications from a medication information card on the smart card by interacting with an identity selector on the provider's computer. The identity selector can transmit the current medications to the drug interaction utility without disclosing any information about the current medications to the provider and without disclosing any information identifying the patient to the drug interaction utility.

17 Claims, 6 Drawing Sheets

AUTOMATICALLY ASSESSING DRUG INTERACTIONS WHILE PROTECTING PATIENT PRIVACY

BACKGROUND

Embodiments of the inventive subject matter generally relate to the field of medicine, and more particularly, to automatically assessing drug interactions while protecting patient privacy.

According to the United States Food and Drug Administration (FDA), adverse drug reactions (ADRs) are the fourth leading cause of death ahead of pulmonary disease, diabetes, pneumonia, and accidents including automobile accidents. The cost of morbidity and mortality from ADRs is estimated to be $136 billion annually. In addition, sixty-four percent of patients who visit to a medical provider receive a prescription. The risk of ADRs increases with the number of medications a patient is taking because of interactions among the medications.

SUMMARY

Embodiments include a method directed to detecting a request, from a medical provider, to analyze drug interactions among a proposed medication and current medications of a patient. In some embodiments, a medication information card can be requested from an identity selector to cause the identity selector to retrieve the medication information card from an electronic device. The medication information card can store data about the patient's current medications. The medication information card can be received from the identity selector. The current medications can be determined from the medication information card. A drug interaction database can be searched for interactions among the proposed and current medications. If there are interactions among the proposed and current medications and information about the current medications should not be disclosed to the medical provider, an indication that there are interactions can be displayed to the medical provider while preserving confidentiality of the current medications.

BRIEF DESCRIPTION OF THE DRAWINGS

The present embodiments may be better understood, and numerous objects, features, and advantages made apparent to those skilled in the art by referencing the accompanying drawings.

DESCRIPTION OF EMBODIMENT(S)

The description that follows includes exemplary systems, methods, techniques, instruction sequences, and computer program products that embody techniques of the present inventive subject matter. However, it is understood that the described embodiments may be practiced without these specific details. For instance, although examples refer to smart cards, embodiments may be implemented on other devices such as Universal Serial Bus (USB) storage devices, mobile phones, personal digital assistants (PDAs), etc. In other instances, well-known instruction instances, protocols, structures, and techniques have not been shown in detail in order not to obfuscate the description.

The risk of ADRs for patients taking multiple medications may be exacerbated if a medical provider is unaware of the medications a patient is taking when prescribing a new medication. In many cases, a patient may not be able disclose their medications to a medical provider. For example, a patient may be unconscious or incapacitated. As another example, a patient may have Alzheimer's or dementia. In other cases, a patient may not wish to disclose medications to a medical provider. For example, a patient may not wish to disclose that they are taking a medication to treat a sexually transmitted disease (STD) to the patient's dentist. Information about a patient's medications may be stored on a smart card or other storage device. When a medical provider wishes to prescribe a medication for the patient, the provider can use a drug interaction utility (e.g., a drug interaction website) to search a drug interaction database for interactions among a proposed medication and the patient's current medications. The drug interaction utility can retrieve the patient's current medications from a medication information card on the smart card by interacting with an identity selector on the provider's computer. The identity selector can transmit the current medications to the drug interaction utility without disclosing any information about the current medications to the provider and without disclosing any information identifying the patient to the drug interaction utility.

Figure 1:
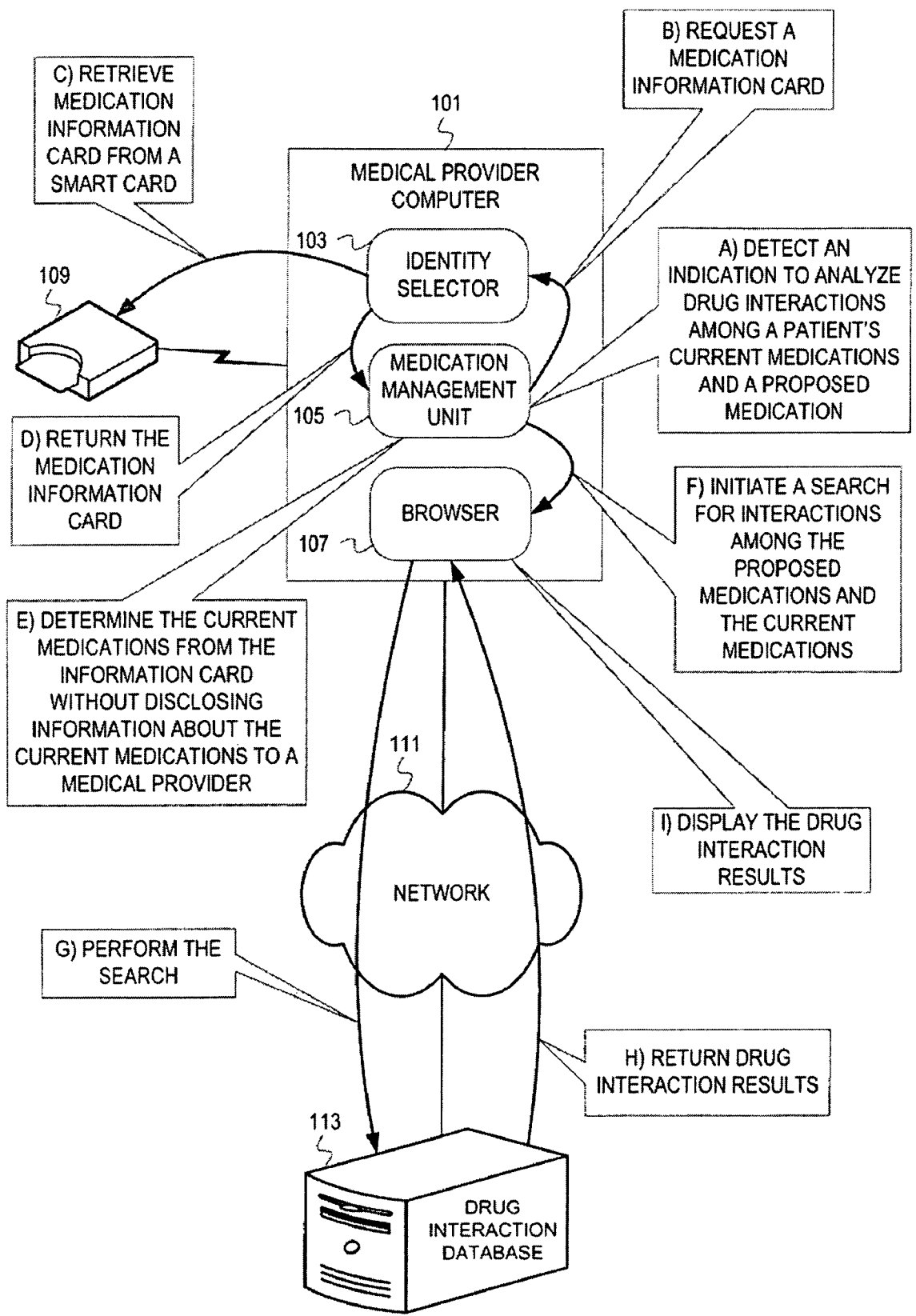
FIG. 1 is an example conceptual diagram of automatically assessing drug interactions among a proposed medication and a patient's current medications while protecting the patient's privacy.

FIG. 1 is an example conceptual diagram of automatically assessing drug interactions among a proposed medication and a patient's current medications while protecting the patient's privacy. A medical provider computer 101 is communicatively coupled with a smart card reader 109 and a network 111. The medical provider computer may communicate with the smart card reader 109 and the network 111 by any suitable wired or wireless connection technology (e.g., Ethernet, 802.11, Bluetooth, USB, etc.). The smart card reader 109 can read the smart card with various techniques (e.g., reading a magnetic strip, radio-frequency identification (RFID), etc.). A drug interaction database 113 is also communicatively coupled to the network 111. The drug interaction database 113 may be hosted on a server in a local area network of the medical provider, hosted on a web server, etc.

The medical provider computer comprises an identity selector 103, a medication management unit 105, and a browser 107. The identity selector 103 allows a user to share data in information cards stored on a smart card with a relying party. The information cards represent the user's multiple identities. Relying parties use data contained in information cards to provide a service (e.g., validating an identity, providing personalized product recommendations, etc.) for the user. In this case, the identity selector 103 facilitates sharing of the patient's medication information card with the medication management unit 105. The information cards may be implemented according to the Information Card Profile V1.0 by Microsoft®.

At stage A, the medication management unit 105 detects an indication from a medical provider to analyze drug interactions among a proposed medication and the patient's current medications. Examples of medical providers include doctors, nurses, nurse practitioners, emergency medical technicians (EMTs), etc. Examples of detecting an indication to analyze drug interactions include detecting a click on a button, detecting a name of the proposed medication typed in a text box, detecting a click on a proposed medication in a list, etc.

At stage B, the medication management unit 105 requests a medication information card belonging to the patient from the identity selector 103. The medication information card includes information about the patient's current medications (e.g., names of the current medications, dosages, lengths of time the current medications have been taken, etc.) and any other information that may influence drug interactions (e.g., age, gender, previous diagnoses, etc). The medication information card may also contain the patient's medical history.

At stage C, the identity selector 103 retrieves the medication information card from a smart card inserted into the smart card reader 109. The identity selector 103 may prompt the patient to choose the medication information card. For example, the patient is prompted to choose the medication information card from multiple information cards existing on the smart card. The identity selector 103 may automatically choose the medication information card. For example, the identity selector 103 chooses a medication information card based on patient profile information indicating a previously used medication information card. Access to the medication information card may be restricted, so the identity selector 103 may request credentials to allow access to the medication information card. Credentials may be provided by the patient. For example, the patient enters a personal identification number. Credentials may be provided by the medical provider. For example, the identity selector 103 may read a digital certificate on the medical provider computer 101. Access permissions may be set by the patient for different types of medical providers to allow medical providers to access the medication information card. For example, the patient may set access permissions to allow emergency medical providers access to the medication information card even if the patient is incapacitated. In addition, the identity selector 103 may allow the patient to specify disclosure permissions. The disclosure permissions indicate what information may be disclosed to the medical provider. For example, the patient may specify that names of the current medications may be disclosed to the medical provider.

At stage D, the identity selector 103 returns the data in the medication information card to the medication management unit 105.

At stage E, the medication management unit 105 determines the current medications from the medication information card data without disclosing information about the current medications to the medical provider if the patient has specified that the information should not be disclosed.

At stage F, the medication management unit 105 initiates a search, on the browser 107, for interactions among the proposed and current medications. Initiating a search can comprise launching the browser, navigating to a drug interaction web site, and specifying the proposed and current medications as search terms. For example, the medication management unit 105 launches the browser 107 and navigates to a medication interaction search engine. The medication management unit passes the proposed medication and the current medications to the search engine via a secured token in response to a request from the search engine. The search engine request may be based on a protocol such as the Information Card Profile V1.0, OpenID®, etc.

At stage G, the browser 107 performs the search on the drug interaction database 113.

At stage H, the drug interaction database 113 returns the drug interaction results. The richness of the drug interaction results can depend on capabilities of the drug interaction website and the disclosure permissions. For example, the drug interaction results may indicate that there are interactions, but may not give specific information as to which of the current medications is causing the interaction if the disclosure permissions do not allow names of the current medications to be disclosed. In addition, the drug interaction website may be able to suggest alternatives to the proposed and/or current medications in the drug interaction results.

At stage I, the browser 107 displays the drug interaction results.

Although examples refer to a medication management unit utilizing a browser to perform a drug interaction search, embodiments are not so limited. For example, a medication management unit may include proprietary software for searching a drug interaction database residing on a medical provider's network. In addition, functionality of the medication management unit may be implemented in a script on a webpage. So, the browser may interact directly with an identity selector to retrieve a medication information card and determine current medications from the medication information card.

Figure 2:
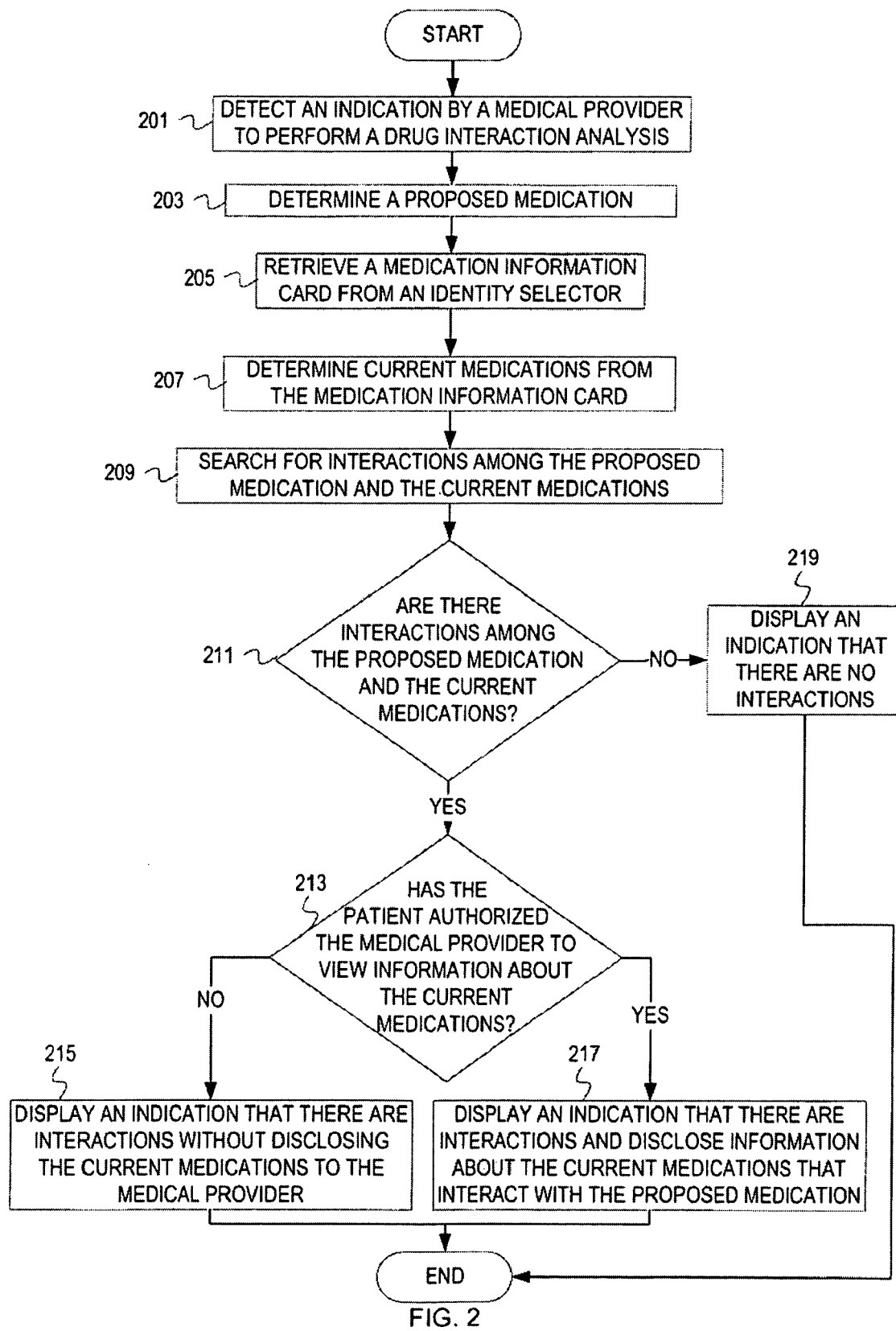
FIG. 2 depicts a flowchart of example operations for automatically assessing drug interactions among a proposed medication and a patient's current medications while protecting the patient's privacy.

FIG. 2 depicts a flowchart of example operations for automatically assessing drug interactions among a proposed medication and a patient's current medications while protecting the patient's privacy. Flow begins at block 201, where an indication by a medical provider to perform a drug interaction analysis is detected. For example, the medical provider enters a new prescription into the patient's electronic medical chart. Flow continues at block 203.

At block 203, a proposed medication is determined. For example, the medical provider is prompted to enter a medication name and dosage information. Flow continues at block 205.

At block 205, a medication information card is retrieved from an identity selector. In response, the identity selector can validate credentials for accessing the medication information card and allow the patient to specify disclosure permissions. Flow continues at block 207.

At block 207, current medications are determined from the medication information card. Flow continues at block 209.

At block 209, a search is performed for interactions among the proposed and the current medications. For example, a medication management unit searches a medical provider's database for drug interactions.

At block 211, it is determined if there are interactions among the proposed and the current medications. If there are interactions, flow continues at block 211. If there are not interactions, flow continues at block 219.

At block 213, it is determined if the patient authorized the medical provider to view information about the current medications. If the patient has not authorized the medical provider to view information about the current medications, flow continues at block 215. If the patient has authorized the medical provider to view information about the current medications, flow continues at block 217.

At block 215, an indication that there are interactions among the proposed and the current medications is displayed to the medical provider without disclosing the current medications to the medical provider.

At block 217, an indication that there are interactions among the proposed and current medications is displayed to the medical provider and information about the current medications that interact with the proposed medication is disclosed to the medical provider.

At block 219, an indication that there are no interactions is displayed to the medical provider.

Although examples refer to a medication interaction management unit running on a medical provider computer, embodiments are not so limited. For example, the medication interaction management unit may be launched from an executable file stored on a smart card.

Figure 3:
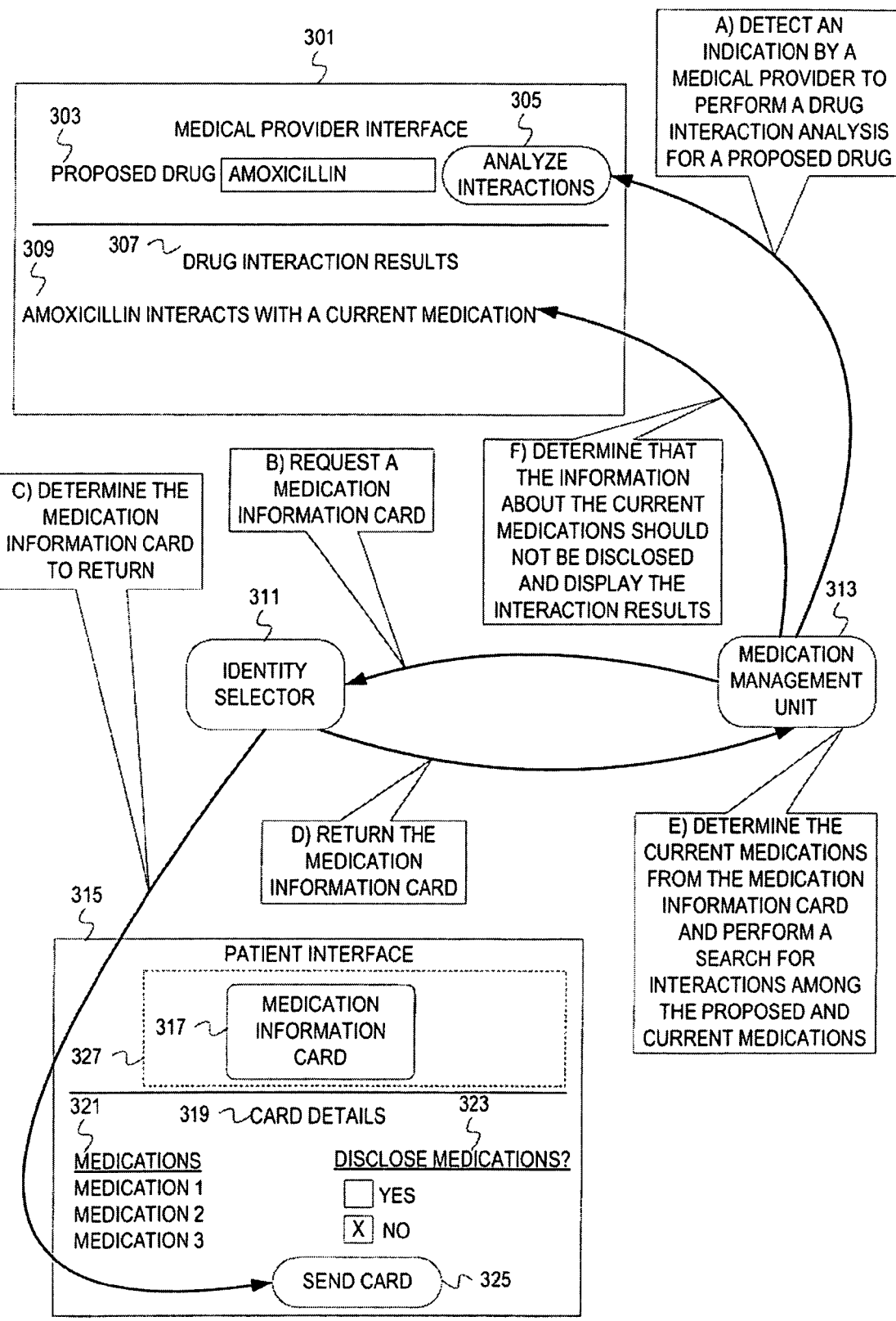
FIG. 3 is an example conceptual diagram of interactions between a medical provider interface and a patient interface.

FIG. 3 is an example conceptual diagram of interactions between a medical provider interface and a patient interface. A medical provider interface 301 comprises a proposed drug input area 303, an analyze drug interaction button 305, and a drug interaction results display area 307. Although the drug input area 303 comprises a text box, other implementations are possible. For example, the drug input area may comprise a list, an expandable menu organized by drug type, etc.

A patient interface 315 comprises an information card display area 327, a card details display area 319, and a send card button 325. The information card display area 327 can display a plurality of information cards existing on a smart card. In this example, one medication information card 317 exists on the smart card. The card details display area 321 displays information stored in a selected information card. In this example, the medication information card 317 is selected and the information stored in the medication information card 317 comprises three current medications as displayed in the card details display area 321 and disclosure permissions 323. Although not shown, the card details display area may allow a patient to change information in the medication information card 317. For example, the patient may delete a medication that the patient is no longer taking, change disclosure permissions 323, etc. In addition, different disclosure permissions 323 may be specified for different providers. For example, a patient may specify that the current medications may be disclosed to the patient's primary care doctor, but may not be disclosed to other medical providers.

At stage A, a medication management unit 313 detects an indication by a medical provider to perform a drug interaction analysis for a proposed drug. In this example, the medication management unit 313 detects a click on the analyze interactions button 305.

At stage B, the medication management unit 313 requests a medication information card from an identity selector 311.

At stage C, the identity selector 311 determines the medication information card to return. In this example, the identity selector 311 displays information cards existing on a smart card in the information card display area 327 and prompts the patient to select the patient's medication information card. The identity selector 311 determines that the medication information card 317 should be returned when the patient clicks the send card button 325.

At stage D, the identity selector 311 returns the medication information card to the medication management unit 313.

At stage E, the medication management unit 313 determines the current medications from data in the medication information card and performs a search for interactions among the proposed and current medications.

At stage F, the medication management unit 313 determines that information about the current medications should not be disclosed to the medical provider based on the disclosure permissions 323, and displays the interaction results in the drug interaction results display area 307. Because the disclosure permissions 323 indicate that information about the current medications should not be disclosed, the interaction results do not include any information about which of the current medications interacted with the proposed medication.

Figure 4:
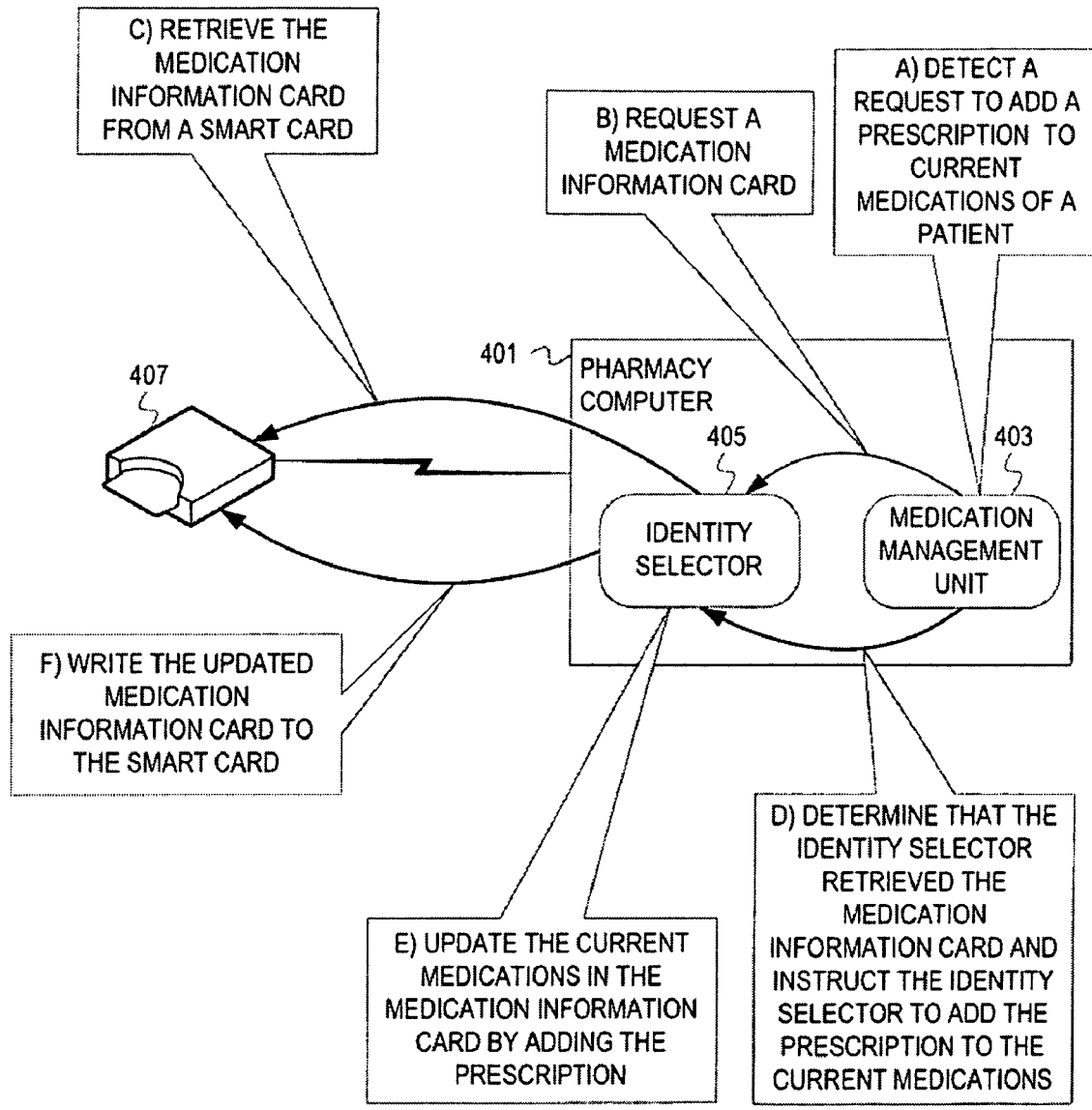
FIG. 4 is an example conceptual diagram of adding a new medication to a patient's current medications on a medical information card.

To be able to analyze interactions among a proposed medication and a patient's current medications, prescriptions should be added to a patient's medication information card. FIG. 4 is an example conceptual diagram of adding a new medication to a patient's current medications on a medical information card. A pharmacy computer 401 comprises an identity selector 405, and a medication management unit 403. The pharmacy computer 401 is communicatively coupled to a smart card reader 407.

At stage A, the medication management unit 403 detects a request to add a prescription to current medications of a patient. For example, the medication management unit 403 detects that a pharmacist entered the prescription into a pharmacy's prescription fulfillment application. In response, the medication management unit 403 may determine that the patient wishes to store medication information on the smart card by prompting the patient via the identity selector 405. In addition, the medication management unit 403 may access the patient's pharmacy record and determine that the patient wishes to store medication information on a smart card.

At stage B, the medication management unit 403 requests a medication information card from the identity selector 405.

At stage C, the identity selector 405 retrieves the medication information card from a smart card. Retrieving the medication information card may comprise prompting the patient to insert the smart card into the smart card reader 407. In addition, the identity selector may request credentials for accessing the card and confirm that the patient wants the prescription to be added to the current medications.

At stage D, the medication management unit 403 determines that the identity selector 405 retrieved the medication information card and instructs the identity selector to add the prescription to the current medications. Determining that the identity selector 405 retrieved the medication information card comprises receiving an indication from the identity selector 405 that the medication information card was successfully retrieved from the smart card.

At stage E, the identity selector updates the current medications in the medication card by adding the prescription.

At stage F, the identity selector writes the updated medication information card to the smart card.

Although examples refer to a pharmacist adding a new medication to a patient's current medications, embodiments are not so limited. For example, a doctor may add a new medication when the doctor gives the patient medication samples. As another example, a patient may add a new medication if the patients pharmacy does not provide that service. The patient may also want to add over-the-counter (OTC) medications and supplements the patient is taking to the current medications because supplements may interact with prescription medications.

Figure 5:
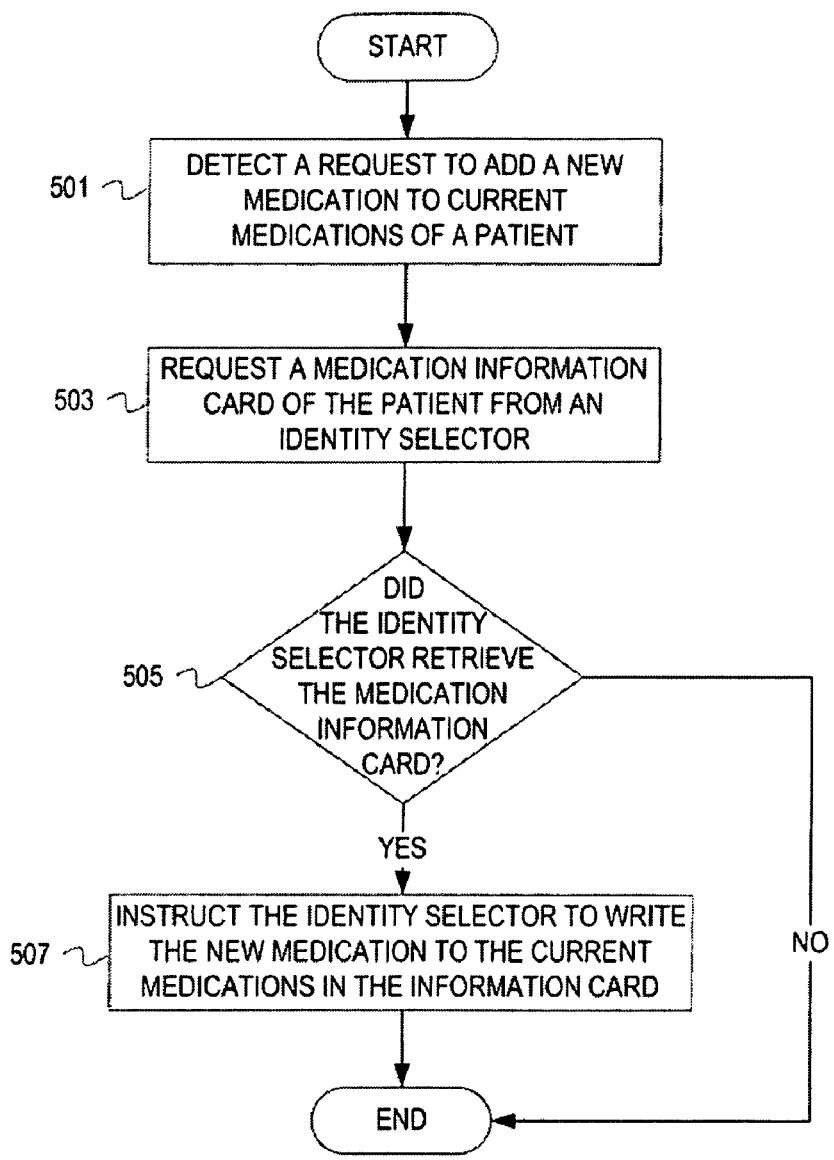
FIG. 5 depicts a flowchart of example operations for adding a new medication to a patient's current medications.

FIG. 5 depicts a flowchart of example operations for adding a new medication to a patient's current medications. Flow begins at block 501, where a request to add a new medication to current medications of a patient is detected. For example, a doctor, who is giving medication samples to the patient, clicks an add medication button after determining that there are no drug interactions. Flow continues at block 503.

At block 503, a medication information card of the patient is requested from an identity selector. In response, the identity selector may determine if the patient wishes to add the new medication to the medication information card. If the patient responds that the new medication should be added, the identity selector can prompt the patient to insert a smart card. The identity selector reads information cards stored on the smart card and can determine the medication information card based on input from the patient or information from a medication management unit. Flow continues at block 505.

At block 505, it is determined if the identity selector retrieved the medication information card. The identity selector may not retrieve a medication information card if the input from the patient indicates that the new medication should not be added to the medication information card. If the identity selector retrieved the medication information card, flow continues at block 507. If the identity selector did not retrieve the medication information card, the flow ends.

At block 507, the identity selector is instructed to write the new medication to the current medications in the information card.

A drug interaction analysis can also be performed when a new medication is added to a patient's current medications. For example, a patient wishes to start taking a supplement. When the patient adds the supplement to the current medications, the patient may indicate that a drug interaction analysis be performed. As another example, a drug interaction analysis may be run at a pharmacy when a patient refills a prescription to determine if it is still safe for the patient to take the prescription.

In addition to allowing a patient to delete medications the patient is no longer taking, medications may also be removed automatically by a medication management unit based on an expiration date. For example, an antibiotic should be taken by a patient for two weeks. At the end of the two weeks, the antibiotic may be automatically deleted from the current medications. Deleted medications may also be archived in the medication information card.

It should be understood that the depicted flowcharts are examples meant to aid in understanding embodiments and should not be used to limit embodiments or limit scope of the claims. Embodiments may perform additional operations, fewer operations, operations in a different order, operations in parallel, and some operations differently. For instance, in FIG. 2, the operation for determining if the patient authorized the medical provider to view information about the current medications may not be performed. So, an indication that there are interactions would be displayed without disclosing the current medications to the medical provider.

Embodiments may take the form of an entirely hardware embodiment, a software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computer system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java®, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (for example, through the Internet using an Internet Service Provider).

Figure 6:
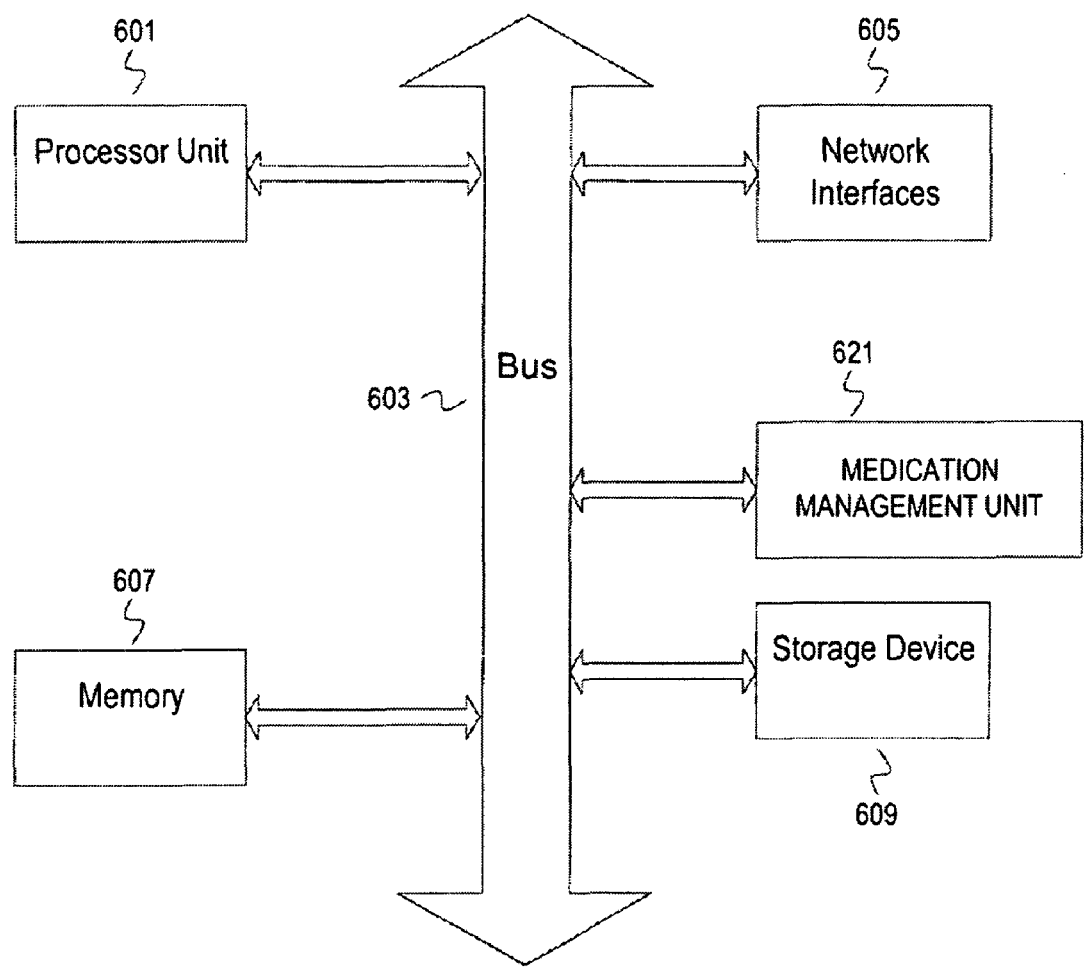
FIG. 6 depicts an example computer system.

FIG. 6 depicts an example computer system. A computer system includes a processor unit 601 (possibly including multiple processors, multiple cores, multiple nodes, and/or implementing multi-threading, etc.). The computer system includes memory 607. The memory 607 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 603 (e.g., PCI, ISA, PCI-Express, HyperTransport®, InfiniBand®, NuBus, etc.), a network interface 605 (e.g., an ATM interface, an Ethernet interface, a Frame Relay interface, SONET interface, wireless interface, etc.), and a storage device(s) 609 (e.g., optical storage, magnetic storage, etc.). The computer system also includes a medication management unit 621 that detects an indication to perform a drug interaction analysis for a proposed medication, retrieves a medication information card, determines current medications from the medication information card, performs a search for interactions among the proposed and current medications, and displays drug interaction results to a medical provider without disclosing information about the current medications. Any one of these functionalities may be partially (or entirely) implemented in hardware and/or on the processing unit 601. For example, the functionality may be implemented with an application specific integrated circuit, in logic implemented in the processing unit 601, in a co-processor on a peripheral device or card, etc. Further, realizations may include fewer or additional components not illustrated in FIG. 6 (e.g., video cards, audio cards, additional network interfaces, peripheral devices, etc.). The processor unit 601, the storage device(s) 609, and the network interface 605 are coupled to the bus 603. Although illustrated as being coupled to the bus 603, the memory 607 may be coupled to the processor unit 601.

While the embodiments are described with reference to various implementations and exploitations, it will be understood that these embodiments are illustrative and that the scope of the inventive subject matter is not limited to them. In general, techniques for automatically assessing drug interactions while protecting patient privacy as described herein may be implemented with facilities consistent with any hardware system or hardware systems. Many variations, modifications, additions, and improvements are possible.

Plural instances may be provided for components, operations, or structures described herein as a single instance.

Finally, boundaries between various components, operations, and data stores are somewhat arbitrary, and particular operations are illustrated in the context of specific illustrative configurations. Other allocations of functionality are envisioned and may fall within the scope of the inventive subject matter. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A computer implemented method for automatically assessing drug interactions while protecting patient privacy, the computer implemented method comprising:
   detecting, by a computer, a request to analyze drug interactions among a proposed medication and a plurality of current medications of a patient;
   requesting, by the computer, a medication information card from an identity selector to cause the identity selector to retrieve the medication information card from a portable electronic device that stores the medication information card in a storage device, wherein the medication information card stores data about the plurality of current medications of the patient, and wherein the medication information card is one of a plurality of medication information cards of the patient stored in the storage device of the portable electronic device that represent multiple identities of the patient;
   receiving, by the computer, the medication information card from the identity selector;
   determining, by the computer, the plurality of current medications from the medication information card;
   searching, by the computer, a drug interaction database for interactions among the proposed medication and the plurality of current medications;
   determining, by the computer, that there are interactions among the proposed medication and the plurality of current medications;
   determining, by the computer, that information about the plurality of current medications is not to be disclosed;
   displaying, by the computer, an indication that there are interactions among the proposed medication and the plurality of current medications while preserving confidentiality of the plurality of current medications;
   suggesting, by the computer, an alternative to the proposed medication based on the interactions among the proposed medication and the plurality of current medications;
   deleting, by the computer, a medication from the plurality of current medications of the patient based on an expiration date associated with the medication to form a deleted medication; and
   archiving, by the computer, the deleted medication in the medication information card stored in the storage device of the portable electronic device.

2. The computer implemented method of claim 1, wherein the portable electronic device that stores the medication information card of the patient comprises one of a smart card, a portable storage device, a mobile phone, and a personal digital assistant.

3. The computer implemented method of claim 1 further comprising:
   detecting, by the computer, a second request, to analyze drug interactions among a second proposed medication and the plurality of current medications of the patient;
   searching, by the computer, the drug interaction database for interactions among the second proposed medication and the plurality of current medications;
   determining, by the computer, that there are interactions among the second proposed medication and the plurality of current medications;
   determining, by the computer, that information about the plurality of current medications is to be disclosed; and
   displaying, by the computer, the interactions along with information about one or more of the plurality of current medications that interacts with the second proposed medication.

4. The computer implemented method of claim 1 further comprising:
   detecting, by the computer, a second request to analyze drug interactions among a second proposed medication and the plurality of current medications of the patient;
   searching, by the computer, the drug interaction database for interactions among the second proposed medication and the plurality of current medications;
   determining, by the computer, that there are no interactions among the second proposed medication and the plurality of current medications; and
   displaying, by the computer, a second indication that there are no interactions.

5. The computer implemented method of claim 1 further comprising:
   detecting, by the computer, a request to add a new medication to the plurality of current medications of the patient;
   determining, by the computer, that the new medication is to be added to the plurality of current medications; and
   instructing, by the computer, the identity selector to write the new medication to the plurality of current medications.

6. The computer implemented method of claim 1, wherein the identity selector retrieves the medication information card from the plurality of medication information cards representing the multiple identities of the patient stored in the portable electronic device based on profile information of the patient.

7. A computer program product stored on a non-transitory computer readable medium having computer usable program code embodied thereon that is executable by a computer to perform a method for automatically assessing drug interactions while protecting patient privacy, comprising:
   detecting, by the computer, a request, to analyze drug interactions among a proposed medication and a plurality of current medications of a patient;
   requesting, by the computer, a medication information card from an identity selector to cause the identity selector to retrieve the medication information card from a portable electronic device that stores the medication information card in a storage device, wherein the medication information card stores data about the plurality of current medications of the patient, and wherein the medication information card is one of a plurality of medication information cards of the patient stored in the storage device of the portable electronic device that represent multiple identities of the patient;
   receiving, by the computer, the medication information card from the identity selector;
   determining, by the computer, the plurality of current medications from the medication information card;
   searching, by the computer, a drug interaction database for interactions among the proposed medication and the plurality of current medications;

determining, by the computer, that there are interactions among the proposed medication and the plurality of current medications;

determining, by the computer, that information about the plurality of current medications is not to be disclosed;

displaying, by the computer, an indication that there are interactions among the proposed medication and the plurality of current medications while preserving confidentiality of the plurality of current medications;

suggesting, by the computer, an alternative to the proposed medication based on the interactions among the proposed medication and the plurality of current medications;

deleting, by the computer, a medication from the plurality of current medications of the patient based on an expiration date associated with the medication to form a deleted medication; and archiving, by the computer, the deleted medication in the medication information card stored in the storage device of the portable electronic device.

8. The computer program product of claim 7, wherein the portable electronic device that stores the medication information card of the patient comprises one of a smart card, a portable storage device, a mobile phone, and a personal digital assistant.

9. The computer program product of claim 7, the method further comprising:
   detecting, by the computer, a second request, to analyze drug interactions among a second proposed medication and the plurality of current medications of the patient;
   searching, by the computer, the drug interaction database for interactions among the second proposed medication and the plurality of current medications;
   determining, by the computer, that there are interactions among the second proposed medication and the plurality of current medications;
   determining, by the computer, that information about the plurality of current medications is to be disclosed; and
   displaying, by the computer, the interactions along with information about one or more of the plurality of current medications that interacts with the second proposed medication.

10. The computer program product of claim 7, the method further comprising:
    detecting, by the computer, a second request to analyze drug interactions among a second proposed medication and the plurality of current medications of the patient;
    searching, by the computer, the drug interaction database for interactions among the second proposed medication and the plurality of current medications;
    determining, by the computer, that there are no interactions among the second proposed medication and the plurality of current medications; and
    displaying, by the computer, a second indication that there are no interactions.

11. The computer program product of claim 7 the method further comprising:
    detecting, by the computer, a request to add a new medication to the plurality of current medications of the patient;
    determining, by the computer, that the new medication is to be added to the plurality of current medications; and
    instructing, by the computer, the identity selector to write the new medication to the plurality of current medications.

12. A computer program product stored on a non-transitory computer readable medium having computer usable program code embodied thereon that is executable by a computer to perform a method for automatically assessing drug interactions while protecting patient privacy, comprising:
    detecting, by the computer, a request to add a new medication to current medications of a patient;
    requesting, by the computer, a medication information card from an identity selector to cause the identity selector to retrieve the medication information card from a portable electronic device that stores the medication information card in a storage device, wherein the medication information card stores data about the current medications of the patient, and wherein the medication information card is one of a plurality of medication information cards of the patient stored in the storage device of the portable electronic device that represent multiple identities of the patient;
    receiving, by the computer, the medication information card from the identity selector;
    determining, by the computer, the current medications from the medication information card;
    searching, by the computer, a drug interaction database for interactions among the new medication and the current medications;
    determining, by the computer, that there are no interactions among the new medication and the current medications;
    instructing, by the computer, the identity selector to write the new medication to the current medications;
    deleting, by the computer, a medication from the current medications of the patient based on an expiration date associated with the medication to form a deleted medication; and
    archiving, by the computer, the deleted medication in the medication information card stored in the storage device of the portable electronic device.

13. A computer system for automatically assessing drug interactions while protecting patient privacy, the computer system comprising:
    a set of one or more processing units;
    a network interface; and
    a storage device having computer usable program code embodied thereon that is executable by the set of one or more processing units to:
      detect a request, to analyze drug interactions among a proposed medication and a plurality of current medications of a patient;
      request a medication information card from an identity selector to cause the identity selector to retrieve the medication information card from a portable electronic device that stores the medication information card in a storage device, wherein the medication information card stores data about the plurality of current medications of the patient, and wherein the medication information card is one of a plurality of medication information cards of the patient stored in the storage device of the portable electronic device that represent multiple identities of the patient;
      receive the medication information card from the identity selector;
      determine the plurality of current medications from the medication information card;
      search a drug interaction database for interactions among the proposed medication and the plurality of current medications;
      determine that there are interactions among the proposed medication and the plurality of current medications;

determine that information about the plurality of current medications is not to be disclosed;

display, an indication that there are interactions among the proposed medication and the plurality of current medications while preserving confidentiality of the plurality of current medications;

suggest an alternative to the proposed medication based on the interactions among the proposed medication and the plurality of current medications;

delete a medication from the plurality of current medications of the patient based on an expiration date associated with the medication to form a deleted medication; and archive the deleted medication in the medication information card stored in the storage device of the portable electronic device.

14. The computer system of claim 13, wherein the portable electronic device that stores the medication information card of the patient comprises one of a smart card, a portable storage device, a mobile phone, and a personal digital assistant.

15. The computer system of claim 13, wherein the set of one or more processing units further executes the computer usable program code to:

detect a second request to analyze drug interactions among a second proposed medication and the plurality of current medications of the patient;

search the drug interaction database for interactions among the second proposed medication and the plurality of current medications;

determine that there are interactions among the second proposed medication and the plurality of current medications;

determine that information about the plurality of current medications is to be disclosed; and display the interactions along with information about one or more of the plurality of current medications that interacts with the second proposed medication.

16. The computer system of claim 13, wherein the set of one or more processing units further executes the computer usable program code to:

detect a second request, to analyze drug interactions among a second proposed medication and the plurality of current medications of the patient;

search the drug interaction database for interactions among the second proposed medication and the plurality of current medications;

determine that there are no interactions among the second proposed medication and the plurality of current medications; and display a second indication that there are no interactions.

17. The computer system of claim 13, wherein the set of one or more processing units further executes the computer usable program code to:

detect a request to add a new medication to the plurality of current medications of the patient;

determine that the new medication is be added to the plurality of current medications; and instruct the identity selector to write the new medication to the plurality of current medications.

* * * * *